United States Patent [19]

Lindstrom et al.

[11] Patent Number: 4,725,586

[45] Date of Patent: * Feb. 16, 1988

[54] SURGICAL SOLUTION

[76] Inventors: Richard L. Lindstrom; Debra Skelnik, both of 20050 Lakeview Ave., Excelsior, Minn. 55331

[*] Notice: The portion of the term of this patent subsequent to Sep. 29, 2004 has been disclaimed.

[21] Appl. No.: 836,156

[22] Filed: Mar. 4, 1986

Related U.S. Application Data

[63] Continuation-in-part of Ser. No. 761,407, Aug. 1, 1985, Pat. No. 4,696,917.

[51] Int. Cl.$^4$ .............................................. A61K 31/70
[52] U.S. Cl. ......................................................... 514/54
[58] Field of Search ............................................ 514/54

[56] References Cited

U.S. PATENT DOCUMENTS 4,486,416 12/1984 Soll et al. ................................ 514/54

OTHER PUBLICATIONS

Kaufman et al., *American Journal of Ophthamology*, 1984, pp. 112-114.

Fisher, *Chemical Abstracts*, 1975, No. 39067r.

Primary Examiner—J. R. Brown
Assistant Examiner—Elli Peselev
Attorney, Agent, or Firm—Hugh D. Jaeger

[57] ABSTRACT

A surgical or irrigation solution which provides the anterior and posterior chamber of the eye with protection during surgical procedures that require irrigation. This irrigation solution is composed of a HEPES buffered Eagle's Minimum Essential Media (MEM) with Earle's Salts, without phenol red, supplemented with mixed isomers of 99% pure, chondroitin sulfate, MEM non-essential amino acids, 2-mercaptoethanol, and sodium pyruvate. Other solutions include a balanced salt solution, chondroitin sulfate, buffers and 2-mercaptoethanol. The solution can also be used in other surgical or medical applications.

13 Claims, No Drawings

SURGICAL SOLUTION

CROSS REFERENCES TO CO-PENDING APPLICATIONS

This application is a continuation-in-part of Ser. No. 761,407, filed Aug. 1, 1985, now U.S. Pat. No. 4,696,917.

BACKGROUND OF THE INVENTION

1. Field of the Invention

The present invention pertains to an intraocular irrigation solution for the anterior and posterior chamber of the eye. The solution also has general surgical applications including orthopedics, such as arthroscopy; urology, such as cystoscopy; neurosurgery; as well as other applications such as in artificial insemination, obstetrics and gynecology (OB/GYN).

2. Description of the Prior Art

There are two intraocular irrigation solutions presently being used in ophthalmic surgeries. These two irrigation solutions are BSS and BSS Plus. BSS is a balanced salt solution that incorporates a sodium citrate and sodium acetate buffering system. BSS Plus consists of a balanced salt solution with a bicarbonate buffering system, with Dextrose added as an additional osmotic agent and energy source. An additional component, oxidized glutathione, is reduced by the ocular cells and serves as an anti-oxidant.

SUMMARY OF THE INVENTION

This intraocular irrigation solution provides the anterior and posterior chamber of the eye protection during surgical procedures that require irrigation. The solutions also can be used as a surgical solution. This irrigation solution specifically protects corneal endothelium in anterior segment surgery. The corneal endothelium and other anterior and posterior chamber structures will be in direct contact with this irrigation solution.

This intraocular irrigation solution includes: 1. A protective coating agent, chondroitin sulfate, a highly negatively charged glycosaminoglycan. Chondroitin sulfate is a naturally occurring, biodegradable material normally found in the human cornea. 2. An effective reducing agent, 2-mercaptoethanol, that can be utilized in both the oxidized and reduced forms by human corneal endothelial cells. Cysteine may well be the limiting amino acid for the synthesis of protein, as well as glutathione. The addition of 2-mercaptoethanol increases the intracellular level of glutathione, and aids in membrane protection and maintenance of cell junctional complexes. 3. An additional buffering agent HEPES (N'-2-hydroxyethylpiperazine-N'-Ethanesulfonic Acid). HEPES buffer tends to stabilize and resist rapid changes in pH in media solutions. The HEPES component will provide a more stable pH for this irrigation solution. Bicarbonate is also found in this irrigation solution, as a necessary buffering component required by ocular cells. 4. An additional substrate, sodium pyruvate, is provided for additional biosynthetic syntheses that may be required by the ocular cells after surgical trauma. 5. The base media of this irrigation solution consists of Eagle's Minimum Essential Media (MEM) supplemented with 1% MEM non-essential amino acids, which is nutritionally complete for ocular cells. The base media can also consist of a balanced salt solution of essential ions and dextrose.

This irrigation solution is designed to protect the anterior and posterior segments of the cornea during surgical procedures, to maintain homoeostasis after surgical trauma, and to provide necessary metabolic substrates that may be needed for wound repair. A completely defined media of Eagle's Minimum Essential media with Earle's salts, without phenol red, is supplemented with a protective agent, chondroitin sulfate; a reducing agent, 2-mercaptoethanol; an alternative energy source, sodium pyruvate; and an additional buffering agent, HEPES; to make a more effective and stable irrigation solution for use in ophthalmic surgeries. Another media is a balanced salt solution with dextrose, and bicarbonate is supplemented with a protective agent, chondroitin sulfate; a reducing agent, 2-mercaptoethanol; an alternative energy source, sodium pyruvate; and an additional buffering agent, HEPES; to make a more effective and stable irrigation solution for use in ophthalmic surgeries or other types of surgeries.

A surgical solution as another embodiment can include a balanced salt solution, chondroitin sulfate, buffers, and 2-mercaptoethanol.

DESCRIPTION OF THE PREFERRED EMBODIMENTS

One irrigation solution is set forth below:

An irrigation solution includes Eagle's Minimum Essential Media with Earle's salts without L-glutamine, and without phenol red (GIBCO), supplemented with 15 mM HEPES buffer, 0.4% chondroitin sulfate, mixed isomers 99.9% pure (SIGMA) with 0.5 mM 2-mercaptoethanol, 1 mM sodium pyruvate and 0.1 mM MEM nonessential amino acids.

The ranges of the compounds include the following. The chondroitin sulfate can be in a range of 0.1% to 5%. The 2-mercaptoethanol can be in a range of 0.001 mM to 1 mM. The HEPES buffer can be in a range of 5 mM to 30 mM. The sodium pyruvate at a range of 0.05 mM to 2 mM and MEM non-essential amino acids at 0.05 mM to 0.2 mM. The sodium bicarbonate, dextrose and sodium pyruvate can be omitted either solely or in combination from the solution.

Additionally, the following compounds can be added as so desired:

1. Ascorbic acid in a range of 0.01–0.2 mM, preferred 0.1 mM;
2. Glutathione in a range of 0.1 ug/ml–5 mg/ml, preferred 0.3 mM;
3. DL-$\gamma$-Tocopherol (Vitamin E) in a range of 0.001 ug/ml–0.1 ug/ml, preferred 0.01 ug/ml;
4. FGF (Fibroblastic Growth Factor) by Collaborative Research, Inc., in a range of 1 ng/ml–10 ug/ml, preferred 10 ng/ml;
5. ECGF (Endothelial Cell Growth Factor) in a range of 200 ng/ml–500 ug/ml, preferred 300 ug/ml; or,
6. Sialic acid in a range of 1 mM–0.001 mM, preferred 0.11 mM.

The base of this intraocular irrigation solution is a completely defined media, supplemented with MEM non-essential amino acids. This replaces the prior art of using a balanced salt solution found in both BSS and BSS Plus.

MODE OF OPERATION

The exposure time to the irrigation solution in normal ophthalmic surgical procedures is normally 3 minutes to less than 1 hour, a very limited time period. But upon special occasions, the anterior chamber is filled with the irrigation solution and allowed to remain there until the aqueous humor is remade, which may take up to 24 hours. During this time, the anterior chamber cells are deprived of necessary nutrients, normally supplied by the aqueous humor. Although the anterior segment cells, most significantly the corneal endothelium, are supplied with nutrients from their basal side, most of the metabolic uptake is from the anterior surface. The corneal endothelium maintains the clarity of the cornea by actively pumping salts and water out of the connective tissue stroma into the anterior chamber of the eye. The $Na^+-K^+$-ATPase pump of these endothelial cells requires ATP and reduced pump sites to keep this pump functional. When the pumping action of these corneal endothelial cells is reduced, the cornea imbibes fluids and becomes thickened and looses optical clarity. Therefore, an irrigation solution with a reducing agent is of considerable advantage. One of the major disadvantages of BSS Plus, with the reducing agent glutathione and the bicarbonate buffering system, is the lack of stability of the solution once prepared. The glutathione component of the irrigation solution is added separately to the solution, and the solution is stable for only a 24 hour period. The buffering ability of the bicarbonate in this irrigation solution is greatly reduced once the solution is exposed to the atmosphere.

The irrigation solution of the present invention effectively deals with these two problems by the addition of 2-mercaptoethanol and an additional HEPES buffering system. 2-mercaptoethanol is an effective reducing agent that can be utilized by human corneal endothelial cells. The HEPES buffering system, in addition to the necessary bicarbonate buffering system, resists rapid changes in the pH of the irrigation solution that may occur with bicarbonate alone. The addition of these two components provides the stable irrigation solution.

Three additional components have been added to the irrigation solution to increase its effectiveness in protecting and repairing the anterior segment of the cornea during and after surgical trauma. Chondroitin sulfate, a highly negatively charged glycosaminoglycan is added to replace any glycosaminoglycan that may be removed from the surface of the corneal endothelial cells from the disruption of aqueous flow or surgical trauma. Glycosaminoglycans are necessary for membrane stability and the maintenance of the three-dimensional structure of receptor proteins. These receptor proteins are required for the metabolic processes of the cell. Chondroitin sulfate acts as a protective coating for the anterior segment cells. An additional substrate, sodium pyruvate, is provided for additional biosynthetic synthesis that may be required by these anterior segment cells after surgical trauma. The third component, MEM non-essential amino acids, are added to supplement the irrigation solution to provide additional amino acids that may be required for wound repair after surgical trauma.

Significant uses of this irrigation solution include: 1. As an ophthalmic irrigating and lubricating eye drop. 2. In the irrigation of burn wounds. 3. As a general irrigation solution for use in surgeries where irrigation is required.

Specific applications in the use of this irrigation solution include: 1. The flushing of ova, and embryos from human and non-human animals in embryo and ova transfer techniques. 2. In vitro fertilization procedures, which includes maintenance of sperm and ova during this procedure. 3. In vitro maintenance of immature and mature ova and embryos. 4. Transfer of ova and embryos back into the recipient uterus.

ALTERNATIVE EMBODIMENTS FOR A SURGICAL SOLUTION

Another embodiment of a surgical solution is now set forth.

A surgical solution includes a balanced salt solution with dextrose, and bicarbonate supplemented with 10 mM HEPES buffer, 0.40% chondroitin sulfate, mixed isomers 99.9% pure (SIGMA) with 0.5 mM 2-mercaptoethanol, and 1 mM sodium pyruvate.

The ranges of the compounds includes the following. The chondroitin sulfate can be in a range of 0.1% to 5%. The 2-mercaptoethanol can be in the range of 0.001 mM to 1 mM. The HEPES buffer can be in a range of 1 mM to 30 mM. The sodium pyruvate can be in a range of 0.05 mM to 2 mM. Cystine in the range of 0.01 mM to 10 mM cystine can also be added to the formulation.

Another example of a balanced salt solution consists of the following:
a. Sodium Chloride 7.14 mg/ml;
b. Potassium Chloride 0.38 mg/ml;
c. 3 mM sodium Phosphate Buffer; $NaH_2PO_4.H_2O$ 0.064 mg/ml; $Na_2HPO_4.7H_2O$ 0.950 mg/ml
d. Sodium Bicarbonate 2.10 mg/ml;
e. Calcium Chloride Dihydrate 0.154 mg/ml;
f. Magnesium Chloride Hexahydrate 0.2 mg/ml;
g. Dextrose 0.92 mg/ml; and,
h. Hydrochloric Acid and/or Sodium Hydroxide (to adjust pH to 7.4) in water for injection.

The base of this surgical intraocular solution is a completely defined balanced salt solution supplemented with dextrose and bicarbonate and with the addition of additional corneal and retinal enhancing agents. These agents are chondroitin sulfate, 2-mercaptoethanol, HEPES buffer and sodium pyruvate. Of course, the sodium bicarbonate, dextrose and sodium pyruvate can be omitted.

A further surgical solution includes a balanced salt solution; 0.1% to 5% chondroitin in sulfate, 99% pure mixed isomers; 1 mM to 30 mM HEPES buffer; 0.001 mM to 1 mM 2-mercaptoethanol; and 0.01 mM to 10 mM sodium phosphate buffer. Likewise, 0.01 mM to 10 mM cystine can also be added to the above formulation. Also, the additional following components of ascorbic acid, glutathione, DL- -Tocopherol, FGF, ECGF, or sialic acid selected individually or combined can likewise be added to any of the alternative embodiments as previously discussed in the Description of the Preferred Embodiments as desired.

Various modifications can be made to the present invention without departing from the apparent scope thereof.

The basic solution by volume for the surgical solution can be the balanced salt solution with or without either the dextrose or sodium bicarbonate. Likewise, other components can be added to the basic baths as desired.

We claim:

1. A composition for irrigating of flushing body tissue during surgical procedures, which composition comprises effective amounts of:
    a. balanced salt solution comprising sodium chloride, potassium chloride, a sodium phosphate buffer system, calcium chloride, and magnesium chloride, the solution having a pH of about 7.4;
    b. chondroitin sulfate;

c. a buffer system based on N'-2-2hydroxyethylpiperazine-N'-ethane sulfonic acid;
d. 2-mercaptoethanol;
e. sodium bicarbonate or dextrose;
f. a pyruvate;
g. a sodium phosphate buffer system; and,
h. cystine.

2. The composition of claim 1 lacking components (e), (f), (g) and (h).

3. The composition of claim 1 lacking components (g) and (h).

4. The composition of claim 1 lacking component (h).

5. The composition of claim 2 in which component (b) is present at a concentration of 0.1–5% by weight, and components (c) and (d) are present at concentrations of about 1 mM–30 mM and 0.001–1 mM, respectively.

6. The composition of claim 2 additionally containing at least one of:
a. ascorbic acid;
b. glutathione;
c. DL-L-tocopherol; or,
d. sialic acid.

7. The composition of claim 6 in which component (a) is present at a concentration of about 0.01–0.2 mM; component (b) is present at about 0.1 ug/ml–5 mg/ml; component (c) is present at about 0.001 ug/ml–0.1 ug/ml; and component (d) is present at about 0.001–1 mM.

8. A method of irrigating or flushing body tissue during surgical procedures which comprises bringing the composition of claim 1 into contact with said tissue.

9. A method of irrigating or flushing body tissue during surgical procedures which comprises bringing the composition of claim 2 into contact with said tissue.

10. A method of irrigating or flushing body tissue during surgical procedures which comprises bringing the composition of claim 3 into contact with said tissue.

11. A method of irrigating or flushing body tissue during surgical procedures which comprises bringing the composition of claim 5 into contact with said tissue.

12. A method of irrigation or flushing body tissue during surgical procedures which comprises bringing the composition of claim 4 into contact with said tissue.

13. A method of irrigating or flushing body tissue during surgical procedures which comprises bringing the composition of claim 6 into contact with said tissue.

* * * * *